US009388236B2

(12) United States Patent
Wells et al.

(10) Patent No.: US 9,388,236 B2
(45) Date of Patent: Jul. 12, 2016

(54) METHODS FOR REDUCING ALLERGIES CAUSED BY ENVIRONMENTAL ALLERGENS

(71) Applicant: Nestec SA, Vevey (CH)

(72) Inventors: George Wells, St. Louis, MO (US); Ebenezer Satyaraj, Wildwood, MO (US)

(73) Assignee: Nestec SA, Vevey (CH)

( * ) Notice: Subject to any disclaimer, the term of this patent is extended or adjusted under 35 U.S.C. 154(b) by 43 days.

(21) Appl. No.: 13/870,374

(22) Filed: Apr. 25, 2013

(65) Prior Publication Data

US 2013/0236475 A1 Sep. 12, 2013

Related U.S. Application Data

(63) Continuation of application No. 12/452,450, filed as application No. PCT/US2008/008405 on Jul. 9, 2008, now Pat. No. 8,454,853.

(60) Provisional application No. 60/958,845, filed on Jul. 9, 2007.

(51) Int. Cl.
A61K 39/395 (2006.01)
A61K 39/00 (2006.01)
G01N 33/53 (2006.01)
C07K 16/18 (2006.01)

(52) U.S. Cl.
CPC ............. C07K 16/18 (2013.01); C07K 2317/76 (2013.01)

(58) Field of Classification Search
None
See application file for complete search history.

(56) References Cited

U.S. PATENT DOCUMENTS

| 6,358,546 | B1 | 3/2002 | Bebiak et al. | |
|---|---|---|---|---|
| 6,504,013 | B1 | 1/2003 | Lawton et al. | |
| 6,849,259 | B2 * | 2/2005 | Haurum et al. | 424/171.1 |
| 8,454,953 | B2 * | 6/2013 | Wells et al. | 424/130.1 |
| 2001/0051155 | A1 * | 12/2001 | Sosin et al. | 424/130.1 |
| 2002/6358548 | | 3/2002 | Bebiak et al. | |
| 2006/0068947 | A1 | 3/2006 | Kempf | |
| 2006/0088926 | A1 * | 4/2006 | Ozawa et al. | 435/266 |
| 2006/0210290 | A1 | 9/2006 | Okuyama | |
| 2006/0210590 | A1 | 9/2006 | Hernandez et al. | |
| 2007/0231341 | A1 * | 10/2007 | McGavin et al. | 424/185.1 |

FOREIGN PATENT DOCUMENTS

| DE | 19523048 C1 * | 12/1996 | B01D 53/84 |
|---|---|---|---|
| GB | 1539102 A | 1/1979 | |
| JP | 62215534 A | 9/1987 | |
| JP | 8-501799 A | 2/1996 | |
| JP | 2004538237 | 12/2004 | |
| JP | 2005-074023 A | 3/2005 | |
| JP | 2005-508361 A | 3/2005 | |
| JP | 2006-166878 A | 6/2006 | |
| WO | 9414475 A1 | 7/1994 | |
| WO | 2003035107 A1 | 1/2003 | |
| WO | 2005074417 A2 | 8/2005 | |
| WO | 2006097530 A2 | 9/2006 | |
| WO | 2007003951 A1 | 1/2007 | |

OTHER PUBLICATIONS

Daugherty et al. 'Formulation and delivery issues for monoclonal antibody therapeutics.' Adv. Drug Deliv. Rev 58:686-706, 2006.*
Arlian et al. 'Distribution and Removal of Cat, Dog, and Mite Allergens on Smooth Surfaces in Homes With and Without Pets.' Pediatrics 110:430, 2002.*
English Translation of the Journal of Immunology, Official Journal of the American Association of Immunologists Mar. 24, 1988.
Carayol et al "Fel d 1 production in the cat skin varies according to anatomical sites," Allergy. 55:570-573, 2000.
Lind, et al. "The Binding of Mouse Hybridoma and Human IgE Antibodies to the Major Fecal Allergen, Der p. I, of Dermatophagiodes pteronyssinus", J. Immunol. 140(12): 4256-4262, Jun. 15, 1988.
Fritsche et al. Prevention of allergic sensitization to beta-lactoglobulin with conjugates made of beta lactobloblin coupled to isologous immunoglobulin G. J. Allergy Clinical Immunology, 93-778-786, Apr. 1994.
Blumenthal et al. "Definition of an Allergen." Allergens and Allergen Immunotherapy, Ed. R. Lockley, S. Bukantz and J. Bousquet. New York: Marcel Decker, 2004: 37-50.
Martyny J.W., et al. "Aerosolozed Sodium Hypochlorite Inhibits Viability and Allergeneicity of Mold on Building Materials" J Allergy Clin Immunol. No. 3 vol. 116 pp. 630-635 Aug. 5, 2005.
Arruda, L.K. et al. "Aspergillus fumigatus Allergen I, a Major IgE-binding Protein, is a Member of the Mitogillin Family of Cytotoxins," J. Exp. Med, vol. 172, pp. 1529-1532 Nov. 1, 1990.
Arbes, S.J. Jr., et al. "Dog Allergen (Can f 1) and Cat Allergen (Fel d 1) in US Homes: Results from the National Survey of Lead and Allergens in Housing", Pediatrics 2005: 116, 542-543.
McKinley, L, et al, Reproducibility of Novel Model of Murine Asthma-Like PUlmonary Inflammation, Clin. Exp. Immunol. 2004; vol. 136, pp. 224-231.
Chapman; M.D. et al. "Monoclonal Antibodies to the Major Feline Allergen Fel d1" J. Immmunol.; vol. 140 pp. 812-818, Feb. 1, 1988.
International Preliminary Report on Patentability and Search Report; PCT/US2008/008405; Jan. 21, 2010.
Extended European Search Report, EP08780052.0, May 17, 2011.
Cases, R. et al. "Cat-Specific IgA Antibodies in Breast Mild from Atopic and Non-Atornic Mothers: Detection of Fel d1-IgG Immune Complexes in Cord Blood and Sera", Int. Arch Allergy Immunol. 118: 317-8, 1999.

(Continued)

Primary Examiner — Nora Rooney
(74) Attorney, Agent, or Firm — Ronald A. Burchett; Julie M. Lappin

(57) ABSTRACT

Compositions suitable for reducing symptoms of an allergic response to environmental allergens comprising molecules that specifically inhibit the ability of the allergen to bind to mast cells in an animal predisposed to having an allergic response to the allergen and methods for reducing such symptoms comprising contacting a source of the environmental allergen with such compositions. Kits, packages, medicaments, and means of communicating about the compositions and methods are also provided.

3 Claims, No Drawings

(56) References Cited

OTHER PUBLICATIONS

English abstract for DE 19523048.
English abstract for JP2004438237.
Tsuji et al, Allergy Induced by Plant Foods, J Jpn Soo Nutr Food Sci 55 303-305 2002. (English abstract at end).
The Journal of Immunology, Official Journal of the American Association of Immunologists Mar. 24, 1988.
English Abstract for JP 2005-074023.
English Abstract for JP 62215534.
English Abstract for JP 2006-166878.
Perzanowski, Matthew S., et al. "The effectiveness of Allerpet/c in reducing the cat allergen Fel d 1", Journal Allergy Clin. Immunol Sep. 1997, pp. 428-430.
Avner, David B., "Evaluation of different techniques for washing cats: Quantitation of allergen removed from the cat and the effect on airborne Fel d 1", Journal Allergy Clin. Immunol Sep. 1997, pp. 307-312.
S Hartwell, "Help I'm Allergic to The Cat", www.stumbleupon.com/su/9LkLIZ; www.messybeast.com/allergy.htm , 1996-2007.

* cited by examiner

METHODS FOR REDUCING ALLERGIES CAUSED BY ENVIRONMENTAL ALLERGENS

CROSS REFERENCE TO RELATED APPLICATIONS

Continuation of U.S. application Ser. No. 12/452,450, now U.S. Pat. No. 8,454,953, filed Dec. 30, 2009 as a national stage application under 35 U.S.C. §371 of PCT/US2008/008405 filed Jul. 9, 2008, claiming priority to U.S. Provisional Application Ser. No. 60/958,845 filed Jul. 9, 2007, the disclosures of each of which are incorporated herein by this reference.

BACKGROUND OF THE INVENTION

1. Field of the Invention

The invention relates generally to compositions and methods for reducing or preventing allergies or their symptoms and specifically to compositions and methods for reducing or preventing allergies or their symptoms caused by environmental allergens.

2. Description of the Related Art

Allergy can be defined as a state of immune responsiveness in an animal to an exogenous antigen (or allergen) that is not otherwise harmful to the animal.

Environmental allergens include allergens that derive from organisms such as plants, molds, animals, and insects. Examples of environmental allergens include plant pollens, and mold spores. Other environmental allergens are found in the excretions of furred animals, and insects, such as mites and cockroaches.

Environmental allergens pose a health threat to people of all ages, most particularly children. The presence of such allergens in the environment can result in symptoms or responses that range from mild rhinitis, to skin problems (e.g., itching and hives), asthma, acute respiratory distress, and even to life-threatening anaphylactic reactions.

Certain environmental allergens, for example, the food allergens from tree nuts and especially peanuts have gained significant attention of the public because of coverage in the popular media. Notwithstanding the greater public awareness, as well as improved understanding of the pathophysiology of allergic responses in sensitized individuals, and improved therapies and treatment modalities, medical researchers have noted an increase of epidemic proportions in recent years in both morbidity and mortality for many of the symptoms and allergic responses noted above in both developing and developed nations. For example, asthma has reportedly increased over the past 2 decades in all age groups, particularly in inner city children. The reasons behind the noted increases are likely multifactorial, but include increased exposure to both indoor and outdoor environmental allergens, as well as improved awareness by both the public and the medical community with resultant increased diagnosis by medical practitioners.

Despite the widespread occurrence of many environmental allergens, major strategies that have been developed as methods for controlling the reactions to such allergens include establishing tolerance, and simple avoidance.

Avoidance strategies have been endorsed by the National Institutes of Health as significant in the treatment or prevention of allergy-induced health problems. Unfortunately, although removal of individuals to "allergen-free mountain institutions or hospitals" resulted in prolonged improvement of the environmental allergen-induced symptoms, it is not practical in many cases that such allergens can be completely avoided, or that allergic persons can afford the time and expense of such institutions. However, it is mildly encouraging that clinical studies show that avoidance of one allergen, even where others are not avoided can result in reduced symptoms, for example, of asthma. Thus, for example, environmental dust mite allergen avoidance successfully mitigated symptoms where mite populations were controlled and related allergen concentrations were lowered at least 100-fold.

Tolerance strategies entail establishment or reestablishment of a nonharmful or more productive response to exogenous allergens. Such an immune state is far more functional than the counter-productive, potentially fatal, over-response of the allergic immune system. Tolerance-inducing strategies have included allergen immunotherapy, wherein the sensitized animal is intentionally exposed to the allergen in a controlled manner, for example through a series of injections, or through oral or nasal absorption. Immunotherapy has been in use for over 100 years, and has been successful, although it may take years to establish an acceptable level of tolerance. A more recent strategy for establishing tolerance involves the use of allergen peptide-based approaches. In some applications, this has involved conjugated or chimeric molecules containing immunostimulatory sequences linked to the allergen. There has been work recently in the area of creating chimeric molecules comprising a portion of human immunoglobulin (IgG Fc) covalently linked to Fel D1. This molecule can essentially paralyze the allergic cell reactivity during treatment, while also inducing tolerance to the Fel D1 in the treated person. The chimeric molecule results in a complex coaggregation of mast cells with basophils the nature of which actively inhibits mediator release, thus minimizing any significant allergic response, even with immunotherapy-inducing doses of the allergen. Tolerance strategies have also employed cellular approaches designed to convert naïve CD4+ T-cell into regulatory T-cells that mitigate a tolerant response to an allergen.

Tolerance strategies, while potentially effective in the specific individual receiving the treatment, are expensive, invasive, time-consuming, and require experts such as doctors, immunologists, and the like, for administration. Treatments for tolerance also involve a certain level of risk associated with adverse reactions and negative outcomes. Further, other animals in the environment that are exposed to the allergen receive no benefit from the treatment—i.e., they are totally individualized. Thus avoidance strategies, where applicable may offer advantages.

Avoidance strategies may be most easily facilitated for allergens that have specific, identifiable point sources. In addition to dust mites, pet allergies are specifically traceable to the pet source. In the case of allergies to cats, although multiple allergens may be present, it has been determined that one specific allergen, Fel D1, is the source of a significant proportion of allergic response in sensitized individuals (Ohman J. L., Lowell F. C. and Bloch K. J. (1974) Allergens of mammalian origin. 111. Properties of major feline allergen. *J. Immunol.* 113: 1668-77). The allergen Fel D1 is shed from the cat's sebaceous glands in the skin, and through cat saliva during grooming. It is a leading cause of cat allergies.

Thus, while cat ownership is on the rise in the United States, allergies to cats have become/remain the primary reason for relinquishment of cats to animal shelters (Scarlett et al., *J. Appl. Animal Welfare Sci.*, 2(1):41-57, 1999). A study of households with cats indicated that Fel D1 is widely present. The allergen was nearly ubiquitous in the house being identified in 96.6% of the beds, 96.9% of bedroom floors, 96.1% of living room floors, and 97.9% of sofas. (Geany et al.,

*Pediatrics*, 116(2): August 2005). Clothing from school children from homes containing cats was tested of school tested outside of the home (in schools), and found to contain Fel D1 antigens. Thus, this environmental antigen poses a substantial risk, not only to sensitized individuals living in households with cats, but to the allergic human population on the whole. (Gorge & Dreborg, *Ped. Allergy Immun.*, 9(1):25-30, 1998).

Fel D1 allergens can be readily detected via in-home ELISA tests. About 14% of children 6 to 19 years of age or older are allergic to cats (NIH news release). Avoidance of Fel D1 could help with owner appeal, pet ownership, and health of children and sensitized pet owners.

Avoidance as a general concept, however, is difficult to embody by practical means. A reduction in the amount of Fel D1, even a minimal reduction, could have substantial impact on the health of sensitized individuals, and could minimize relinquishment as a result of a person in home becoming sensitized. To date, strategies for reducing Fel D1 have included physical isolation or removal, for example by keeping the allergic person in a clean space that is not occupied by the cat, or through regular bathing of the subject cat to minimize Fel D1 dispersal.

In another approach for physically removing Fel D1 from the environment, cats genetically modified so as to not produce Fel D1 are now available on the market. These engineered cats lack the gene to produce the allergenic form of Fel D1, and instead produce a different, non-allergenic protein. While this approach may prove effective, it remains relatively untested and nothing is publicly-known about the long-term health and vigor of the resultant cats. Further, the available types and selection of such genetically-altered cats is very limited. In addition, the animals are very expensive, ranging from about $3,000 to $5,000 ($U.S.).

To aid in considering strategies for addressing environmental allergen issue, it is instructive to have an understanding of allergic reactions in the immune system. The allergic response begins with sensitization that results in production of allergen specific IgE-antibodies. For example, when an allergen is inhaled, antigen presenting cells in the airway mucosa, internalize, and process the allergen. The allergens are then expressed on their cell surface and are then presented to other immune cells, particularly T-lymphocytes. As a result, B-lymphocytes are transformed into antibody secretory plasma cells. In an allergic response, the plasma cell produces IgE antibodies that have specific binding for a specific allergen. Once in circulation, IgE binds to high affinity receptors on mast cells, basophils, Langerhans cells, and activated monocytes. Such binding leaves the IgE's allergen-specific receptor site free for further interaction with the same allergen.

Upon re-exposure to the allergen, binding of the allergen to IgE initiates a rapid and intense response from the immune system. Cross-linking of mast cell/basophil/bound IgE antibodies by allergen begins an intracellular signaling cascade, which causes degranulation of immune cells, and concomitant release of inflammation mediators. Mast cells regulate their IgE receptor expression to keep the number of unoccupied IgE receptor sites constant. Circulating IgE antibodies bind to these receptor sites, waiting for their specific allergen to be encountered.

The immune system's response to allergen exposure can be divided into immediate hypersensitivity or early phase reaction, that occurs within 15 minutes of exposure to the allergen, and a second, or late phase reaction that occurs 4-6 hours after the disappearance of the first phase symptoms and can last for days or even weeks. The early phase is characterized by mediators released by mast cells including histamine, prostaglandins, leukotrienes, and thromboxane. These generate responses characteristic of an allergies in tissue local to the IgE and mast cells. Sneezing, swelling and congestion, nasal blockage, bronchoconstriction, coughing and wheezing are well-known effects. The late phase reaction can be characterized by cellular infiltration, fibrin deposition and tissue destruction in the lung, leading to increased bronchial reactivity, oedema and inflammation. Thus, the interaction of allergen, IgE, and mast cells is central to the immune system's response and results in the triggering of mast cell mediator release, leading directly to both the early and late phase reactions.

WO07113633A2 discloses methods for reducing the amount of Fel D1 shed by a cat by administering to a cat an immunogenic composition comprising at least one Fel D1 polypeptide or its fragment or a polynucleotide molecule encoding Fel D1 polypeptide. US2006000474180 discloses fusion proteins comprising an allergen sequence such as those for Fel D1 linked via an IgG hinge region to another polypeptide sequence capable of specifically binding to a native IgG inhibitory receptor containing an immune receptor tyrosine based inhibitory motif (ITIM). WO06097530A2 discloses medicaments for treating cat allergy comprising a virus-like or virus core particle, with first attachment site, and specific feline protein antigen, with second attachment site, covalently linked via the sites.

Recent advances in methods of antibody production may allow alternative means for avoiding environmental antigens that cause allergy in sensitized individuals. For example, milk-based antibody systems and egg based antibody systems, e.g., US20030003133A1 discloses using milk as a carrier for allergens for inducing oral tolerance to cat dander and other allergens.

Thus, there is a need in the art for compositions and methods useful for reducing environmental allergens and thereby reducing, minimizing or even preventing an allergic response, or symptoms of such a response, in an animal predisposed to having such a response when exposed to the allergen.

SUMMARY OF THE INVENTION

It is, therefore, an object of the present invention to reduce, minimize, or prevent allergies caused by environmental allergens.

It is a further object of the invention to provide compositions and methods for reducing, minimizing, or even preventing at least one symptom of an allergic reaction in a sensitized animal.

It is yet a further object of the invention to provide articles of manufacture in the form of kits that contain combinations of compositions, food products or compositions, and other compounds, and devices useful for reducing or preventing allergic responses to an environmental allergen.

One or more of these and other objects are achieved using novel compositions and methods that utilize at least one molecule that specifically inhibits the ability of the allergen to bind to mast cells in an animal predisposed to having an allergic response to the allergen.

These, other, and further objects can be also be achieved using methods for reducing, in an animal, an allergic response to an allergen in an environment. The method comprises minimizing exposure to the allergen in an animal predisposed to having an allergic response to the allergen by contacting a source of the allergen in the environment with a composition containing a molecule that inhibits the ability of the allergen to bind to mast cells in the animal predisposed to having an allergic response to the allergen; thereby reducing the allergic response in the animal to the allergen in the environment.

Other and further objects, features, and advantages of the present invention will be readily apparent to those skilled in the art.

DETAILED DESCRIPTION OF THE INVENTION

Definitions

As used herein, the term "allergy" is synonymous with "allergic response" or "allergic reaction." Each of the terms refers to a state of immune responsiveness in an animal specific to an exogenous antigen (or "allergen") that is not otherwise harmful to the animal. A "symptom" of an allergic response refers to any measure of the aforesaid immune responsiveness, e.g., on the molecular level (including measurement of an activity or expression of a protein, or transcript or gene), the cellular level, organ level, systemic level, or organism level. Such symptoms can comprise one or more such levels. Symptoms may include generalized phenomena such as inflammation, respiratory complaints, swelling, or distress typically associated with allergy, rhinitis, edema, and allergic skin disorders including but not limited to atopic dermatitis (e.g., eczema), urticaria (e.g., hives) and angioedema, and allergic contact dermatitis. More specific phenomena that are "symptoms" of an allergic response include any measurable or observable change, for example at the cellular level, including but not limited to local or systemic changes in cell populations, eosinophilia, recruitment and/or activation of immune cells, including, for example, mast cells and/or basophils, changes in antigen-presenting cells (including but not limited to FcεRI-bearing dendritic cells), intracellular or molecular changes, including measurement or observations of one or more steps in an immunological cascade, release of intracellular compounds that mediate an allergic response (e.g., mediators), and changes in one or more cytokines (e.g., IL-3, IL-5, IL-9, IL-4, or IL-13) or related compounds or antagonists thereof. The skilled artisan will understand that certain symptoms as defined herein as more readily measured than others, and some are measured through subjective assessment or self-assessment of the symptom. For other symptoms, there are convenient or rapid assays or measurements for objectively assessing changes.

The term "animal" as used herein includes both humans and non-human animals of any species or kind, including, for example, avian, bovine, canine, equine, feline, hierine, murine, ovine, porcine, and simian animals. References to "animals" herein in one context means any animal susceptible to or suffering from an allergic response to an environmental antigen, or at least one symptom of such an allergic response upon exposure to the allergen. In another context an "animal" can include any animal that is the source or a source of an environmental allergen. It will be clear from any given usage of term which context is intended, the animal having an allergy, or an animal that is a source of an allergen.

Animals can be sources of environmental allergens in any number of ways. For example, allergens may be disseminated in or with hair or skin or skin cells, such as dead, dying, flaking skin, skin cells, or skin debris. Such allergens may include dander from various animals. In addition, the waste products from an animal, including feces and/or urine may include one or more allergens for sensitive individuals. Animals may also produce and or secrete certain allergens in other bodily fluids, such as saliva. Allergens that contained within, produced in, or transmitted or disseminated through saliva are sometimes referred to herein as "orally disseminated" allergens, although such allergens may also be disseminated by other, non-oral means. Animals may also harbor, bear, or carry certain pests such as insects, microorganisms (e.g., bacteria, yeasts, or mold), or parasites any of which can be a direct source of an allergen, or may cause the animal to directly or indirectly shed more skin, hair or other potential allergens, or may cause a change in the animal's health status so as to produce an allergen, or more or an allergen. And while animal hair in many cases may not be highly allergenic per se, such hair can be a source of allergens such as pollen, dust, mold and the like, which are then dispersed into the environment. The methods disclosed herein are particularly useful for mitigating allergic responses to the presence of companion animals such as canines and felines.

The term "environment" as used herein refers to a local environment of an animal, for example for a human a house, room, car, office, hotel, yard, garage, and the like, could each be "environments" as used herein. Further, any area exposed to a source of an allergen such as a pet, insect, or plant, can be considered to be an environment for purposes herein. Although environments are frequently indoors, nothing herein precludes a limited area partially or completely open or outdoors to be an environment, for example a patio, deck, landing, lanai, gazebo, porch, or the like can constitute an environment for purposes herein. The environment can also comprise a part or all of an animal, plant, insect, or other source of an allergen. For example, providing a composition or treatment for oral intake to an animal that is the source of an allergen constitutes treating the "environment" of another animal that is allergic or predisposed to having an allergic reaction to the allergen.

As used herein, an "allergy treatment" also referred to at times herein as an "allergy medication" means any compound, composition, food, or drug useful for reducing, minimizing, preventing, or treating an allergic response to an antigen in an animal, or for mitigating the symptoms, or at least one symptom of such an allergy in an animal.

The term "individual" means an individual animal of any species or kind.

The term "antibody" as used herein includes polyclonal and monoclonal antibodies of any type and from any species, as well as immunoglobulin fragments such as Fv, Fab, Fab', $F(ab')_2$, or other antigen-binding antibody fragments, sequences or subsequences that interact with molecular specificity (e.g., demonstrate specific binding) with an antigen.

The term "single package" means that the components of a kit are physically associated in or with one or more containers and considered a unit for manufacture, distribution, sale, or use. Containers include, but are not limited to, bags, boxes or cartons, bottles, packages of any type, design, or material, over-wrap, shrink-wrap, affixed components (e.g., stapled, adhered, or the like), or combinations of any of the foregoing. For example, a single package kit may provide containers of individual compositions and/or food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain, for example, instructions on how to use the kit, or safety or technical information about one or more components of a kit. Examples of information that can be provided a part of a virtual kit include instructions for use, safety information such as material safety data sheets, poison control information, information on potential adverse reaction, clinical study results, and the like, dietary information such as food composition, or caloric composition, general information on treating allergies, or general information on maintaining an environment free or relatively free of specific environmental allergens, or minimizing specific allergens in an environment.

All percentages expressed herein are by weight of the composition on a dry matter basis unless specifically stated otherwise. The skilled artisan will appreciate that the term "dry matter basis" means that an ingredient's concentration in a composition is measured after any free moisture in the composition is removed.

As used throughout, ranges are used herein as shorthand, so as to avoid having to set out at length and describe each and every value within the range. Any appropriate value within the range can be selected, where appropriate, as the upper value, lower value, or the terminus of the range.

Dosages expressed herein are in milligrams per kilogram of body weight per day (mg/kg/day) unless expressed otherwise.

The term "microorganism" means bacteria, molds and other fungi, and yeasts.

As used herein and in the appended claims, the singular form of a word includes the plural, and vice versa, unless the context clearly dictates otherwise. Thus, the references "a," "an," and "the" are generally inclusive of the plurals of the respective terms. For example, reference to "a puppy", "a method", or "a food" includes a plurality of such "puppies", "methods", or "foods". Reference herein for example to "an antibody" includes a plurality of such antibodies, whereas reference to "pieces" includes a single piece. Similarly, the words "comprise", "comprises", and "comprising" are to be interpreted inclusively rather than exclusively.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to and does not limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by controlling law. The discussion of those references is intended merely to summarize the assertions made therein. No admission is made that any such patents, patent applications, publications or references, or any portion thereof is relevant, material, or prior art. The right to challenge the accuracy and pertinence of any assertion of such patents, patent applications, publications, and other references as relevant, material, or prior art is specifically reserved.

The Invention

Generally, in various aspects, the invention provides compositions, methods, devices, and kits useful for reducing or preventing allergies or symptoms of allergic reactions to allergens that are present in a sensitized animal's environment. The compositions provide molecules that generally prevent binding of the allergen to mast cells in the sensitized animal. One preferred embodiment uses molecules that are able to specifically bind the allergen, for example an antibody specific for the allergen, to treat a source of the allergen. For example, the molecule is used to treat a surface where the allergen is present, or the air in a specific environment, or an animal that is a source of the allergen. In one preferred embodiment, the allergen is orally disseminated from an animal and the compositions are provided as a food composition to the animal that is the source of the orally-disseminated allergen. The molecule in the composition specifically binds the allergen present, in the animal's mouth before it is released into the environment thus preventing or minimizing the release of the free allergen into the environment of the sensitive animal. The bound form of the allergen is unable to bind to mast cells in a sensitive animal's immune system and thus cannot induce the symptom or the allergic response. For example, many humans are allergic to allergens secreted from the mouth of felines. The felines lick their body, contact objects in their environment, and disseminate the allergen to such objects. Humans contact the objects having the allergen and develop an allergic reaction. Exposing the feline's mouth to a composition of the present invention binds the allergen before it contacts the human and prevents it from causing the allergenic reaction in the human even if the human is exposed to the bound allergen. A bound allergen cannot interact with the mast cells in the human and cause an allergenic reaction.

More specifically, in a first aspect, the invention provides compositions suitable for reducing at least one symptom of an allergic response to an allergen in an environment. The compositions preferably comprise at least one molecule that inhibits the ability of the allergen to bind to mast cells in an animal predisposed to having an allergic response to the allergen. As used herein, "reducing at least one symptom" includes reducing such symptoms before they occur so that there are no symptoms to an allergic response and thus preventing the allergic response.

Several types of molecules are useful in accordance with the compositions provided herein. In one embodiment, the molecule binds to the allergen with a high degree of specificity. For example, antibodies, aptamers, and agonists/antagonists of the allergen are useful herein. Portions of such molecules, such as antigen binding fragments (Fab) of antibodies, are also useful herein. Any molecule or portion or fragment thereof that retains binding specificity for the allergen can be used as the molecule provided in the compositions, or a part of the molecule where such molecule is a chimera of two or more portions linked together, for example, covalently.

In one embodiment, the compositions further comprise one or more additional components or ingredients to provide further functionality. Thus, one or more of a flavoring, a fragrance, a stabilizer, a surfactant, a binder, or a detergent may be present in the compositions in various embodiments. As will be described, the compositions are generally not intended for vaccinating or directly treating the animal having the allergy, although there is no intention to exclude such possibilities in certain embodiments. Rather, the compositions are intended generally to treat the environment generally, or one or more specific sources, such as a point source, of an environmental allergen. In a particular embodiment, the compositions are provided orally, for example with or as food, to an animal or insect that is a source of the allergen.

In one embodiment, the compositions are useful where the allergen is from a human, dog, cat, mite, cockroach, plant, or microorganism. Other types and sources of allergens can be addressed with the compositions provided herein, for example allergens from other animals not specifically enumerated, other insects, or other sources altogether.

In one embodiment, the allergen is Fel D1, Can f1, Der p1 Der p2, Bla g1, Bla g2, Asf 1, Ara h1, Ara h2, or Ara h3. These allergens are each of significance in terms of their prevalence or the public's actual or potential exposure to them in the environment in homes, offices, hotels, restaurants, shopping malls and retail centers, schools, and other public or private spaces.

In one embodiment, at least a portion of the molecule is specific for the allergen. In another embodiment, at least a portion of the molecule comprises an antibody, an aptamer, or an agonist, or part of any of the foregoing, that binds specifically to the allergen, in one embodiment comprising an antibody, or binding portion or fragment of an antibody, or other binding-specific protein or peptide, the antibody or other binding molecule is produced through biotechnological means, such as by large scale fermentation of a microorganism, through production in a readily obtained animal product, such as the milk or egg of an animal, or by production in a plant or crop (e.g., so-called "plantibodies"). Such large-scale production techniques for the manufacture of antibodies will help to ensure that an economical and abundant supply of antibodies or other molecules is available for use in the compositions of the invention. The skilled artisan will appreciate that the production techniques for making the binding molecule in sufficient quantities are available and can be implemented using knowledge known the art to enable economic use in the compositions described.

In a preferred embodiment, antibodies are produced by immunizing an avian such as a chicken with and antigen that causes production of the antibodies in eggs. The antibodies can be separated from the egg and administered to the animal or the eggs, or a part of the eggs such as the egg yolk, can be applied directly onto or admixed with a food or other composition suitable for administration to an animal. Methods for preparing antibodies using avian eggs and for administering avian eggs containing antibodies, particularly in food compositions, are well known to skilled artisans, e.g., U.S. Pat. No. 6,413,515, U.S. Pat. No. 5,080,895, U.S. Pat. No. 4,748,018, and references cited therein.

In a particular embodiment, antigens that cause eggs to produce anti-Fel D1 antibodies are used to immunize an avian, preferably a chicken; the avian eggs containing anti-Fel D1 antibodies are collected and optionally processed to enrich the concentration of the antibodies; the eggs or processed eggs are admixed with or applied to a food suitable for a cat; the food containing the antibodies is fed to the cat; and the antibodies complex with Fel D1 antigens in the mouth of the cat, thus neutralizing the antigenicity of the Fel D1 antigen and reducing or preventing allergies or their symptoms when an allergic animal comes into contact with the cat or the cat's environment, particularly objects that have been licked by or otherwise contacted by the cat in a manner that would leave Fel D1 allergens on the objects.

In another embodiment, the composition comprises a molecule that is at least in part a choatropic agent, a detergent, or a salt. In yet another embodiment, the molecule modifies pH. In still other embodiments, compositions are provided in which the molecule destroys protein epitopes involved in binding of the allergen to mast cells, the molecule comprising a proteolytic activity, a binding-activated modified protein complex, or a ligand that binds irreversibly to the allergen.

In one embodiment the composition is edible. The composition can be readily mixed with food of any type for provision to an animal. A human caretaker can administer the compositions with food to an animal under the human's care. The compositions can also be formulated to contain or provide a portion of the macronutrient and micronutrient requirements for an animal and can be provided as a replacement for, or a supplement to, the animal's regular diet. The composition can be provided as, added to, or mixed with a snack, treat, chew, or other supplement to the normal intake of food, and can be formulated to be provided one or multiple times per day, week or other time period. The composition can also be provided as an addition to the animal's liquid intake, for example, in or with its drinking water. For purposes of clarity, it should be noted that such edible compositions are not provided to the animal that has the allergic response, for example as an oral vaccine, or to orally induce a degree of tolerance to the allergen. Rather, the edible compositions described herein are provided preferably directly to an animal that is the source or a source of environmental allergen.

In a preferred embodiment, the allergen is Fel D1 and the molecule comprises an antibody specific for Fel D1. In the case of an edible composition of such embodiment, the composition is provided to a cat for consumption as food, supplement, or in drinking water. The Fel D1 antigen is at least significantly orally disseminated, for example in or with a cat's saliva. The oral intake of the compositions provided herein will reduce, preferably substantially reduce or even completely eliminate the local dissemination of allergen-inducing forms of Fel D1. Preferably, the composition will result in binding or inactivation of the allergen either before it is disseminated or shortly thereafter.

In one embodiment, the molecule comprises a chimeric protein. In one embodiment, the molecule comprises at least a binding portion of an antibody to the allergen fused to at least a portion of an IgG molecule. For example, at least a portion of an anti-Fel D1 antibody that specifically binds to Fel D1, fused to at least a portion of an IgG molecule. Such molecules are potentially especially useful because in addition to binding the environmental allergen to prevent the mast cell interaction, to the extent they are introduced into the sensitized animal from the environment, they will help to induce some measure of tolerance in the allergic animal, particularly where the IgG portion of the molecule is derived from the same species as the allergic animal. Thus, in the ease of treating a home of a person allergic to a pet cat, the chimeric molecule will inactivate the environmental Fel D1, and potentially induce some tolerance to the allergen through the presence of the IgG portion and the bound Fel D1 antigen when the sensitized person is exposed to the complexed, or bound, Fel D1.

In another aspect, rather than mixing with, or adding to a food, the compositions are provided as food products comprising a composition of the present invention. In one embodiment, the food product is formulated for a household pet, the allergen is an orally-disseminated allergen from the pet, and the molecule comprises at least a portion of an antibody that specifically binds the allergen. In a preferred embodiment, the pet food product is formulated for a feline. In one example of a food product formulated for the feline, the allergen to be bound by the composition is Fel D1. In some examples multiple allergens from the same source can be targeted in a single food composition. As discussed above, the food composition can be fed once or multiple times per day, or once or multiple time per week, or in any regular or irregular periodic treatment. The food composition can be provided as either a replacement for, or supplement to the animal's normal diet. In certain embodiments, the food composition is in the form of a treat, chew, snack, or the like. The food composition can be provided in the form of a fluid, or with a fluid for intake. For example, a food composition can be formulated to readily dissolve in, form a suspension with, or mix with, the animal's drinking water, or other fluid or beverage for intake. For such purposes, it may be useful to formulate as a solid, tablet, powder, liquid, liquid concentrate, gel, or in another suitable form for direct use, or for dilution prior to administration to the animal. For some applications, the food composition can be provided in the form of a treat or "lick" or block that is provided to the animal and encourages the animal to frequently or periodically lick the composition, thus ensuring that the animal will frequently be reexposed to the molecule that prevents the allergen from binding to mast cells in the sensitive individual.

In another of its several aspects, the present invention provides methods for reducing, minimizing, or preventing at least one symptom of an allergic response to an environmental allergen. The methods generally comprise contacting an environmental allergen with one or more antibodies or other molecules that bind to the allergen and prevent the allergen from inducing an allergic reaction in an animal susceptible to or suffering from allergies caused by the allergen.

Thus, in one embodiment, the invention provides methods for reducing an allergic response to an allergen in an environment in an animal predisposed to having an allergic response to the allergen. The methods comprise contacting a source of the allergen with a composition containing a molecule that inhibits the ability of the allergen to bind to mast cells in the animal. The molecule binds to the allergen and prevents or reduces the allergic response in the animal to the environmental allergen. Essentially, the methods comprise minimizing exposure to the allergen in an animal that is predisposed to having an allergic response to the allergen.

In one embodiment the animal predisposed to having the allergic response is human, feline, or canine. Preferably the animal is a human.

In one embodiment, the environment of interest is a home, an office, an overnight accommodation, a yard, a retail facility, or any portion of the foregoing. In one embodiment the environment is any of the foregoing and the source of the allergen is a different animal, such as a pet or pest in the human's home.

In another embodiment, the allergen is from a human, dog, cat, insect, plant, or microorganism. In preferred embodiments, the allergen is Fel D1, Can f1, Der p1 Der p2, Bla g1, Bla g2, Asf 1, Ara h1, Ara h2, or Ara h3.

In one embodiment, the molecule is an antibody. As with the compositions, the antibody can be produced via any of several means that will generate useful quantities of antibodies for use in the methods. In a preferred embodiment, the antibody is produced by immunizing a chicken with and antigen that causes production, of the antibody in eggs produced by the chicken. The eggs can be applied directly onto or admixed with a food or other composition suitable for administration to an animal.

In one embodiment, the composition for use in the method is in the form of an aerosol, a liquid, a gel, a semisolid, a solid, or a powder. In certain embodiments, the composition is applied to a surface in the environment, for example by spraying, misting, wiping, shaking, dusting, depositing, or other method of application to a surface. In one embodiment, the surface is the surface of an animal that is a source of the allergen. For such applications, the treatment can be applied for example as a skin or hair treatment, such as a cream, lotion, ointment, moisturizer, gel, soap, shampoo, deodorant, powder, oral rinse, mouthwash, dentifrice or other oral or dental treatment including polish, paste, wash, or the like.

In one embodiment, the allergen is from an animal and the composition is consumed by that animal. In one embodiment, the animal is the sole or major source of the allergen in the environment. The animal in one embodiment is a different species than the animal that is predisposed to having an allergic response to the allergen.

In a preferred embodiment, the allergen is Fel D1 from a feline, the molecule comprises an anti-Fel D1 antibody, and the composition is consumed by a feline.

In one embodiment, the molecule is a hybrid molecule comprising at least a binding portion of an antibody to the allergen and at least a portion of an immune protein, such as an IgG. In such embodiments, the immune protein can be completely unrelated to the allergen. For example, in one embodiment, the allergen is a feline allergen, particularly the feline allergen Fel D1, and the animal having the allergic response is a human. For such purposes, in this embodiment, the molecule is a chimera of at least a binding portion of an antibody to Fel D1, and at least a portion of human IgG.

In a further aspect the present invention provides kits suitable for treating an environmental allergen with a composition. In one embodiment, the kits comprise, in separate containers, in a single package, or in separate containers in a virtual package, as appropriate for the kit component, at least one composition comprising at least one molecule that inhibits the ability of the allergen to bind to mast cells in an animal predisposed to having an allergic response to the allergen and at least one of (1) one or more ingredients suitable for consumption by an animal that is at least a source of an environmental allergen, (2) a palatant, flavoring, fragrance, or other additive to make the composition, or the composition mixed with food or drink more palatable or appealing before, during, or after preparation or consumption, to the consumer, purchaser, or caregiver, (3) one or more nutrients or supplements that promote health, or minimize production or transport or dissemination of an allergen by an animal that is a source of the allergen, and (4) one or more drugs or other materials suitable for preventing or treating allergies or allergic symptoms, and (5) instructions for using the compositions and optional components of the kits, particularly for alleviating or preventing the allergic response in the sensitive animal, for example in accordance with the methods provided herein. When the kit comprises a virtual package, the kit is limited to instructions in a virtual environment in combination with one or more physical kit components.

In one embodiment, the kit comprises an edible form of a composition described herein in a sachet or pouch attached to a food composition, such as a pet food package, along with instructions for mixing the edible composition into the food, adding the composition to the food, or dissolving, mixing, or adding the composition to a fluid that is to be administered to the animal receiving the food, such as drinking water. In another embodiment, the kit comprises at least a food composition described herein comprising the molecule that binds that allergen, along with instructions for use. In another kit, a concentrated form of the composition is provided, and also provided is a tool or device for conveniently measuring a suitable amount of the concentrate for mixing with, adding to, diluting, or dissolving with a food or fluid to be provided to the animal that is the source of the allergen being treated. In a presently preferred embodiment of these kits, the allergen is Fel D1, and the composition provided comprises at least a binding portion of an anti-Fel D1 antibody that binds to the Fel D1 antigen in a feline's mouth when red to the feline. In one embodiment, the composition comprising the molecule—e.g., an anti-Fel D1 antibody, and the other edible kit components are admixed in accordance with the instructions prior to consumption by an animal, typically just prior to such consumption. In one kit, the composition in edible form is provided in a convenient dosage in a series of identical packages, such that one package of the composition is added to one package (e.g., can) of pet food without a requirement for measuring. Such kits can be provided such that for each package of pet food in a point-of-sale package, there is one package of edible antibody-containing composition provided. For example, twelve cans of food and twelve packages of composition are packaged together in a single kit.

In another embodiment, the kit comprises a composition, in concentrated or other form, instructions for use, including, if required, instructions for preparation of a suitable dilution, and optionally one or more of a diluent or extender, a tool or measuring device for preparing a suitable dilution, and an applicator such as a sprayer, duster, wipe, or the like. Such kits may be useful for compositions formulated for treating surfaces, for treating the air in an environment, or for treating an animal with a composition for external use.

For all such kits, the kits may include devices, applicators, dilutors, and the like that are automatic or that automate the dosing, dilution, mixing, addition, or application of the composition for an appropriate use. For any of the kits described herein, they can be provided as sachets or bundled with other products to maximize convenience, compliance, and efficiency of use and purchase. Thus, if the allergen is from a pet, the kits can include, or be bundled with any or all of food for the pet, bedding for pet, shampoo or cosmetic items for the pet, medicine for the pet. Where the allergen is of insect or plant origin, the kits may include appropriate additional products such as insecticides or other treatments, including for example laundry detergents and products for minimizing house dust mite infestations, or with products for minimizing treating or mitigating pollen or "hayfever" type allergies. The kits may also include, or be attached as sachets or the like with, allergy treatments or medications provided for the animal with the allergic response to the allergen.

Any of the foregoing kits, as well as others can also be provided as virtual kits. When the kit comprises a virtual package, the kit provides instructions in a virtual environment in combination with one or more physical kit components, such as those described above. The kit contains at least one composition described herein, and other components, including optional components. The kits may contain the kit components in any of various combinations and/or mixtures. In one embodiment, the kit contains a packet containing one or more compositions and a container of food for consumption by an animal. The kit may contain additional items such as a device for mixing the compositions and ingredients or a device for containing the admixture, e.g., a food bowl. In another embodiment, the compositions are mixed with additional nutritional supplements such as vitamins and minerals that promote good health in an animal. Further information and instructions are provided in the virtual environment that is provided to the purchaser—i.e., directions to a website, faxback server, or an included computer readable device such as a CD-ROM.

In another aspect, the invention provides a communication means, or a means for communicating information about or instructions for one or more of (1) using allergen-specific molecules to minimize, reduce, or prevent allergic responses to an environmental allergen, for example by minimizing, reducing, or preventing interaction of the allergen with mast cells; (2) admixing the compositions comprising such allergen-specific molecule (e.g., Abs) with the other components so as to minimize, reduce, or prevent an allergic response in an animal disposed to having such an allergic response; (3) administering the allergen-specific molecules, alone or in a composition to an animal that is a source of an allergen, alone or in combination with the other elements of the present invention, and (4) using the kits provided herein for minimizing, reducing, or preventing an allergic response in an animal predisposed to having an allergic response.

The communication means comprises one or more of text information, audio information, still or moving images, including animations, or video. In various embodiments, the communication means comprises one or more of a printed document, a static or dynamic electronic document, for example a hypertext document, a computer readable or digital storage medium, including but not limited to electronic, optical, or magnetic media of any type, audio information, an audio, audiovisual or visual display or presentation, or video information however encoded, wherein the communication means displays or contains information or instructions comprising any of the aforesaid. In certain embodiments, the communication means comprises a web site, an FAQ (Frequently Asked Questions) page or file, an electronic file or collection of two or more electronic files of the same or different types, an email or email file, a visual display, kiosk, brochure, advertisement, package or product label, package or product insert, handout, public announcement, audiotape or electronic audio file embodied in any machine-readable or computer-readable medium, a videotape, videodisk, or electronic video file embodied in any machine readable or computer-readable medium, DVD, CD-ROM, or the like, or any combination of the foregoing containing such information or instructions. Useful information includes one or more of (1) methods and techniques for combining and administering the allergen-specific molecules and/or other components, (2) contact information for allergic animals or their guardians or caregivers to use if they have a question about the kit, the composition, or its use; (3) nutritional information about food compositions, and other components provided in any kit, (4) safety information including for example emergency information, and further contacts in the event of adverse reaction; poison control, material data safety sheets, (5) information useful for reordering, for example through automatic fulfillment systems; (6) general information about allergies, environmental allergens, and methods for minimizing or eliminating specific environmental allergens. Useful instructions can include amounts for mixing and administration amounts and frequency. The communication means is useful for instructing on the benefits of using the present invention and communicating the approved methods for administering the invention to an animal.

Another aspect of the invention provides a package comprising a material suitable for containing a food composition adapted for consumption by an animal that is a source of allergen, for example a feline or canine food composition, as provided herein. The package has affixed thereto a label containing a word or words, picture, symbol, design, acronym, slogan, phrase, or other device, or combination thereof (the label "device"), that indicates that the contents of the package contains a food composition adapted for consumption by an animal that is a source of an environmental allergen. Typically, such label device comprises the words "formulated for allergy-causing animals", "formulated for allergen-bearing animals" or an equivalent expression printed on the package. Any package or packaging material suitable for containing food, food compositions, food ingredients, or the like is useful herein, e.g., a bag, box or carton, bottle, can, pouch, and the like manufactured from paper, plastic, foil, metal, and the like, or a combination of any of the foregoing. In a preferred embodiment, the package contains a food composition adapted for reducing at least allergic response to an environmental allergen in an animal predisposed to having such response by providing a molecule that prevents the allergen from binding to mast cells in the animal predisposed to having the allergic reaction.

In a further aspect, the invention provides for a use of composition comprising at least one molecule that inhibits the ability of the allergen to bind to mast cells in an animal predisposed to having an allergic response to the allergen to prepare a medicament. The composition can be a dietary composition but is preferably an antibody. In another, the invention provides for the use of such composition to prepare a medicament for reducing an allergic response in an animal to an allergen in an environment. Generally, medicaments are prepared by admixing dietary components, compounds, or compositions, with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

EXAMPLES

Various aspects of the invention can be further illustrated by the following examples. It will be understood that these examples are provided merely for purposes of illustration and do not limit the scope of the invention disclosed herein unless otherwise specifically indicated.

Example 1

Cat saliva containing the allergen Fel D1 was incubated with different concentrations of antibodies at 37° C. for 60 minutes or with PBS as control [labeled 'None']. Two different antibodies were used (1) antibody made against complete Fel D1 protein ("Indoor Ab"), or (2) antibody made against specific peptides found in Fel D1 protein ("FG1 Ab"). The antibodies were tested for their ability to block binding of the allergen to human IgE. After incubating, the ability of Fel D1 to bind human IgE was tested in an ELISA system using human plasma, including plasma with Fel D1-specific-IgE. Three different kinds of human serum were used in the testing: (1) Fel D1 plasma: plasma obtained from cat-allergic individuals having Fel D1-specific IgE, (2) Other Allergic Plasma: plasma from individuals with allergies other than allergies to cats (IgE is present in the serum, but not Fel D1-specific IgE), and (3) Non-allergic plasma: obtained from non-allergic individuals with low levels of IgE. When Fel D1 binds to human IgE in the ELISA system used, a very high signal is obtained. The signal measured was absorbance at 450 nm.

TABLE 1

| Source of Antibody (dilution) | Fel D1 plasma | Other allergic plasma | Non allergic plasma |
| --- | --- | --- | --- |
| Indoor (1:20) | 0.1125 | 0.0825 | 0.0805 |
| Indoor Ab (1:200) | 0.094 | 0.074 | 0.071 |
| Indoor Ab (1:2000) | 0.11 | 0.0765 | 0.0715 |
| FGI Ab (1:20) | 0.866 | 0.071 | 0.08 |
| FGI Ab (1:200) | 0.8585 | 0.0795 | 0.0745 |
| FGI Ab (1:2000) | 0.837 | 0.078 | 0.0785 |
| Control (PBS only) | 0.8815 | 0.075 | 0.0785 |

As seen in Table 1, cat saliva containing Fel D1 pre-incubated with PBS alone as control binds well to human IgE in Fel D1 plasma, giving a high signal [0.88]. Even in the absence of anti-Fel D1 antibody, the cat saliva containing Fel D1 antigen did not generate a signal with the nonspecific sera obtained from individuals not having specific allergic responses to cats. This confirms that the high signal observed with the Fel D1-specific-human IgE is specific binding of the allergen. It was also observed that this specific binding can be blocked by incubating the cat saliva containing the Fel D1 with polyclonal antibody made against the whole Fel D1 protein. As see in the Table 1, the signal obtained in the Control reaction ("Control", Table 1) of 0.88 dropped to less than 0.12 when the saliva containing the Fel D1 was pre-incubated with different concentration of the 'Indoor Ab.' As can be seen from the Table, the blocking phenomenon was specific because incubation of the saliva containing Fel D1 with the antibody FG1 Ab did not interfere with binding to human IgE, i.e., there was no blocking.

To further explore the nature of the blocking of the binding of Fel D1 to the human IgE observed after incubation with the anti-Fel D1 polyclonal antibody. Indoor Antibody, the experiment was repeated with greater dilutions of the blocking Indoor Antibody. As shown in Table 2, the extent of blocking was a function of the dilution of the antibody. At dilutions of 1:2000, substantial reduction of signal was observed as in the prior experiment, indicating that the preincubation with antibody blocked the ability of the allergen Fel D1 to bind to the IgE. However, the blocking was diminished with increasing dilution of antibody. Under these test conditions, when Fel D1 was pre-incubated with 'Indoor Ab' diluted to greater than 1:200,000, binding to human IgE was substantially restored.

TABLE 2

| Experimental Details | Average Signal Fel D1 positive plasma | Average Signal Other allergic plasma | Average Signal Non allergic plasma |
| --- | --- | --- | --- |
| 1:2,000 dilution | 0.124 | 0.106 | 0.116 |
| 1:20,000 dilution | 0.183 | 0.096 | 0.104 |
| 1:200,000 dilution | 0.421 | 0.096 | 0.113 |
| 1:2,000,000 dilution | 0.518 | 0.124 | 0.104 |
| 1:20,000,000 dilution | 0.523 | 0.106 | 0.120 |
| 1:200,000,000 dilution | 0.493 | 0.104 | 0.122 |
| 1:2000,000,000 dilution | 0.529 | 0.095 | 0.117 |
| No blocking Ab | 0.456 | 0.121 | 0.112 |

Referring to Tables 1 and 2, the data clearly show specific block binding of Fel D1 to human IgE using very low concentration of Fel D1 specific antibody. Binding of allergen to human IgE present on pre-sensitized mast cells is the primary trigger for allergic reaction. Blocking the ability of allergen to bind to IgE can thus avoid this trigger, and minimize, reduce, or even prevent an allergic response in an allergic individual. It is also useful to reiterate that in these experiments, the incubation of Fel D1 with, the anti-Fel D1 antibody was done not only in its native form, but in its native matrix of cat saliva.

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A method for reducing an allergic response in a human to Fel D1 in an environment comprising minimizing exposure to Fel D1 in the human predisposed to having an allergic response to Fel D1 by contacting the Fel D1 in the environment with a composition containing an anti-Fel D1 polyclonal antibody that inhibits the ability of Fel D1 to bind to mast cells in the human predisposed to having an allergic response to Fel D1; thereby reducing the allergic response in the human to the Fel D1 in the environment, wherein the Fel D1 in the environment is on a surface of an object that has been contacted by the cat and the composition is applied directly to the surface, wherein the composition is a liquid, aerosol, or gel, and the anti-Fel D1 polyclonal antibody is present at a concentration greater than 1:200,000 dilution.

2. The method of claim 1, wherein the composition is applied directly to the surface by a method selected from pouring, spraying, misting, wiping, shaking, dusting or depositing the composition onto the surface.

3. The method of claim 1, wherein the surface is a solid surface.

\* \* \* \* \*